(12) United States Patent
Lecuivre et al.

(10) Patent No.: US 9,801,705 B2
(45) Date of Patent: Oct. 31, 2017

(54) HERNIA PROSTHESIS

(71) Applicant: Sofradim Production, Trévoux (FR)

(72) Inventors: Julie Lecuivre, Jassans-Riottier (FR); Sebastien Ladet, Caluire & Cuire (FR)

(73) Assignee: Sofradim Production, Trévoux (FR)

( * ) Notice: Subject to any disclaimer, the term of this patent is extended or adjusted under 35 U.S.C. 154(b) by 159 days.

(21) Appl. No.: 14/397,212

(22) PCT Filed: Jun. 28, 2013

(86) PCT No.: PCT/EP2013/063643
§ 371 (c)(1),
(2) Date: Oct. 27, 2014

(87) PCT Pub. No.: WO2014/001508
PCT Pub. Date: Jan. 3, 2014

(65) Prior Publication Data
US 2015/0080918 A1    Mar. 19, 2015

(30) Foreign Application Priority Data

Jun. 29, 2012  (FR) ...................... 12 56206

(51) Int. Cl.
*A61F 2/00* (2006.01)
*D04B 21/12* (2006.01)

(52) U.S. Cl.
CPC ............ *A61F 2/0063* (2013.01); *D04B 21/12* (2013.01); *A61F 2210/0076* (2013.01); *A61F 2220/0016* (2013.01); *A61F 2250/005* (2013.01); *D10B 2509/08* (2013.01)

(58) Field of Classification Search
CPC ............ A61F 2/0063; A61F 2002/0068; A61F 2250/005; A61F 2210/0076; A61F 2220/0008; A61F 2220/0016; D04B 21/12
See application file for complete search history.

(56) References Cited

U.S. PATENT DOCUMENTS

| | | |
|---|---|---|
| 3,054,406 A | 9/1962 | Usher |
| 3,276,448 A | 10/1966 | Usher |
| 3,718,725 A | 2/1973 | Hamano |
| 3,887,699 A | 6/1975 | Yolles |
| 4,767,628 A | 8/1988 | Hutchinson |

(Continued)

FOREIGN PATENT DOCUMENTS

| | | |
|---|---|---|
| CN | 201879864 U | 6/2011 |
| EP | 1055757 A1 | 11/2000 |

(Continued)

OTHER PUBLICATIONS

Chinese Office Action, Application No. 2012800347410 dated Mar. 30, 2015.

(Continued)

*Primary Examiner* — Todd J Scherbel

(57) ABSTRACT

The present invention relates to a prosthesis (200) comprising:—at least one layer of a flexible mesh (1) delimited by a peripheral outer edge (1*a*), said mesh having a first color, and—at least one layer (2) of porous material fixed to said mesh substantially along the perimeter of said peripheral outer edge, said layer of porous material being recessed at its central part (4), said layer of porous material having a second color, different from said first color.

22 Claims, 5 Drawing Sheets

(56) References Cited

U.S. PATENT DOCUMENTS

Figure 1:
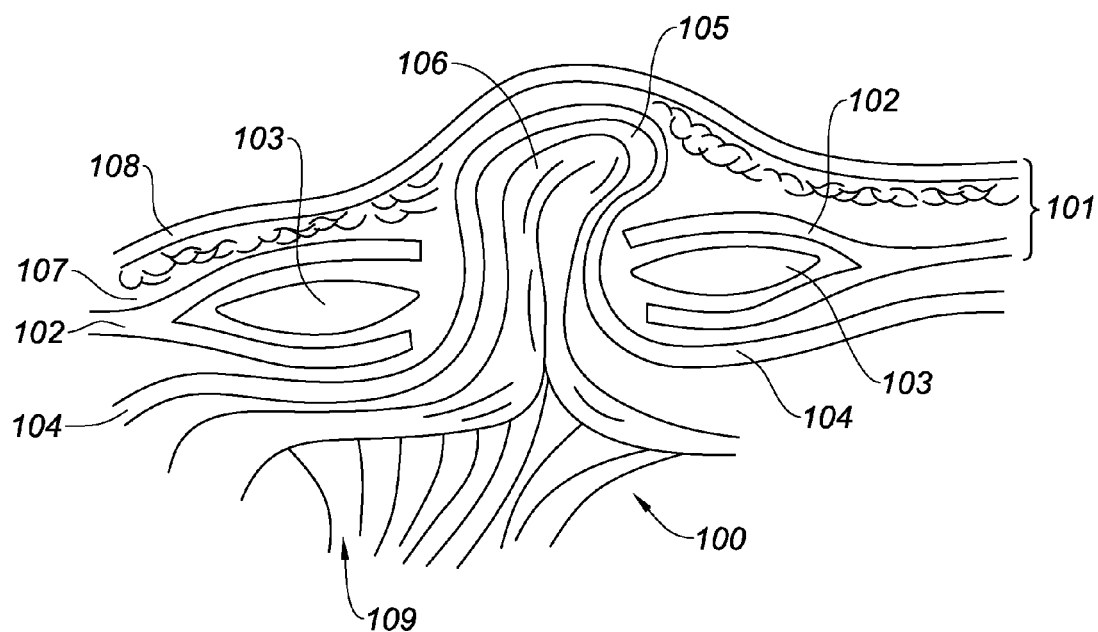

| | | |
|---|---|---|
| 4,931,546 A | 6/1990 | Tardy et al. |
| 4,976,737 A | 12/1990 | Leake |
| 5,106,629 A | 4/1992 | Cartmell et al. |
| 5,116,357 A | 5/1992 | Eberbach |
| 5,147,374 A | 9/1992 | Fernandez |
| 5,195,542 A | 3/1993 | Gazielly et al. |
| 5,201,745 A | 4/1993 | Tayot et al. |
| 5,254,133 A | 10/1993 | Seid |
| 5,258,000 A | 11/1993 | Gianturco |
| 5,368,602 A | 11/1994 | de la Torre |
| 5,370,650 A | 12/1994 | Tovey et al. |
| 5,397,331 A | 3/1995 | Himpens et al. |
| 5,593,441 A | 1/1997 | Lichtenstein et al. |
| 5,634,931 A | 6/1997 | Kugel |
| 5,676,967 A | 10/1997 | Williams et al. |
| 5,695,525 A | 12/1997 | Mulhauser et al. |
| 5,702,416 A | 12/1997 | Kieturakis et al. |
| 5,711,960 A | 1/1998 | Shikinami |
| 5,743,917 A | 4/1998 | Saxon |
| 5,766,246 A | 6/1998 | Mulhauser et al. |
| 5,769,864 A | 6/1998 | Kugel |
| 5,916,225 A | 6/1999 | Kugel |
| 5,919,232 A | 7/1999 | Chaffringeon et al. |
| 5,922,026 A | 7/1999 | Chin |
| 6,042,534 A | 3/2000 | Gellman et al. |
| 6,090,116 A | 7/2000 | D'Aversa et al. |
| 6,113,623 A | 9/2000 | Sgro |
| 6,120,539 A | 9/2000 | Eldridge et al. |
| 6,162,962 A | 12/2000 | Hinsch et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,180,848 B1 | 1/2001 | Flament et al. |
| 6,197,935 B1 | 3/2001 | Doillon et al. |
| 6,201,439 B1 | 3/2001 | Ishida et al. |
| 6,214,020 B1 | 4/2001 | Mulhauser et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,270,792 B1 | 8/2001 | Guillemet et al. |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,079 B1 | 10/2001 | Trabucco |
| 6,319,264 B1 | 11/2001 | Tormala et al. |
| 6,383,201 B1 | 5/2002 | Dong |
| 6,391,060 B1 | 5/2002 | Ory et al. |
| 6,425,924 B1 | 7/2002 | Rousseau |
| 6,447,551 B1 | 9/2002 | Goldmann |
| 6,485,503 B2 | 11/2002 | Jacobs et al. |
| 6,500,777 B1 | 12/2002 | Wiseman et al. |
| 6,596,002 B2 | 7/2003 | Therin et al. |
| 6,610,006 B1 | 8/2003 | Amid et al. |
| 6,616,685 B2 | 9/2003 | Rousseau |
| 6,645,226 B1 | 11/2003 | Jacobs et al. |
| 6,652,595 B1 | 11/2003 | Nicolo |
| 6,669,735 B1 | 12/2003 | Pelissier |
| 6,712,859 B2 | 3/2004 | Rousseau et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,746,458 B1 | 6/2004 | Cloud |
| 6,755,868 B2 | 6/2004 | Rousseau |
| 6,790,213 B2 | 9/2004 | Cherok et al. |
| 6,800,082 B2 | 10/2004 | Rousseau |
| 6,872,227 B2 | 3/2005 | Sump et al. |
| 6,926,723 B1 | 8/2005 | Mulhauser et al. |
| 7,011,688 B2 | 3/2006 | Gryska et al. |
| 7,021,086 B2 | 4/2006 | Ory et al. |
| 7,022,358 B2 | 4/2006 | Eckmayer et al. |
| 7,041,868 B2 | 5/2006 | Greene et al. |
| 7,060,103 B2 | 6/2006 | Carr, Jr. et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,101,381 B2 | 9/2006 | Ford et al. |
| 7,156,804 B2 | 1/2007 | Nicolo |
| 7,156,858 B2 | 1/2007 | Schuldt-Hempe et al. |
| 7,252,837 B2 | 8/2007 | Guo et al. |
| 7,279,177 B2 | 10/2007 | Looney et al. |
| 7,291,294 B2 | 11/2007 | Stolpe et al. |
| 7,331,199 B2 | 2/2008 | Ory et al. |
| 7,393,319 B2 | 7/2008 | Merade et al. |
| 7,404,199 B2 | 7/2008 | Arneson et al. |
| 7,556,598 B2 | 7/2009 | Rao |
| 7,594,921 B2 | 9/2009 | Browning |
| 7,614,258 B2 | 11/2009 | Cherok et al. |
| 7,732,354 B2 | 6/2010 | Fricke et al. |
| 7,785,334 B2 | 8/2010 | Ford et al. |
| 7,789,888 B2 | 9/2010 | Bartee et al. |
| 7,806,905 B2 | 10/2010 | Ford et al. |
| 7,824,420 B2 | 11/2010 | Eldridge et al. |
| 7,828,854 B2 | 11/2010 | Rousseau et al. |
| 7,869,861 B2 | 1/2011 | Moctezuma de la Barrera et al. |
| 7,900,484 B2 | 3/2011 | Cherok et al. |
| 8,100,924 B2 | 1/2012 | Browning |
| 8,123,817 B2 | 2/2012 | Intoccia et al. |
| 8,157,821 B2 | 4/2012 | Browning |
| 8,157,822 B2 | 4/2012 | Browning |
| 8,182,545 B2 | 5/2012 | Cherok et al. |
| 8,206,632 B2 | 6/2012 | Rousseau et al. |
| 8,215,310 B2 | 7/2012 | Browning |
| 8,562,633 B2 | 10/2013 | Cully et al. |
| 8,682,052 B2 | 3/2014 | Fitz et al. |
| 8,758,800 B2 | 6/2014 | Stopek et al. |
| 2002/0087174 A1 | 7/2002 | Capello |
| 2002/0099344 A1 | 7/2002 | Hessel et al. |
| 2002/0131988 A1 | 9/2002 | Foster et al. |
| 2002/0165601 A1 | 11/2002 | Clerc |
| 2003/0130745 A1 | 7/2003 | Cherok et al. |
| 2004/0098118 A1 | 5/2004 | Granada et al. |
| 2004/0215219 A1 | 10/2004 | Eldridge et al. |
| 2004/0224007 A1 | 11/2004 | Zhang |
| 2005/0113849 A1 | 5/2005 | Popadiuk et al. |
| 2005/0240261 A1 | 10/2005 | Rakos et al. |
| 2005/0244455 A1 | 11/2005 | Greenawalt |
| 2005/0261782 A1 | 11/2005 | Hoganson |
| 2006/0025785 A1 | 2/2006 | Cully et al. |
| 2006/0034887 A1 | 2/2006 | Pelissier |
| 2006/0116696 A1 | 6/2006 | Odermatt et al. |
| 2006/0121078 A1 | 6/2006 | Trogolo et al. |
| 2006/0188546 A1 | 8/2006 | Giroux |
| 2006/0224038 A1 | 10/2006 | Rao |
| 2006/0253203 A1 | 11/2006 | Alvarado |
| 2006/0282103 A1 | 12/2006 | Fricke et al. |
| 2007/0088391 A1 | 4/2007 | McAlexander et al. |
| 2007/0129736 A1 | 6/2007 | Solecki |
| 2007/0198040 A1 | 8/2007 | Buevich et al. |
| 2007/0244548 A1 | 10/2007 | Myers et al. |
| 2007/0260268 A1 | 11/2007 | Bartee et al. |
| 2007/0299538 A1 | 12/2007 | Roeber |
| 2008/0017200 A1 | 1/2008 | Carepa et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0161837 A1 | 7/2008 | Toso et al. |
| 2008/0172071 A1 | 7/2008 | Barker |
| 2008/0199506 A1 | 8/2008 | Horres et al. |
| 2008/0255593 A1 | 10/2008 | St-Germain |
| 2009/0036995 A1 | 2/2009 | Lozier et al. |
| 2009/0036996 A1 | 2/2009 | Roeber |
| 2009/0069826 A1 | 3/2009 | Walther et al. |
| 2009/0082792 A1 | 3/2009 | Koyfman et al. |
| 2009/0105526 A1 | 4/2009 | Piroli Torelli et al. |
| 2009/0125107 A1 | 5/2009 | Maxwell |
| 2009/0142385 A1 | 6/2009 | Gross et al. |
| 2009/0163936 A1 | 6/2009 | Yang et al. |
| 2009/0171377 A1 | 7/2009 | Intoccia et al. |
| 2009/0187197 A1 | 7/2009 | Roeber et al. |
| 2009/0192530 A1 | 7/2009 | Adzich et al. |

(56) References Cited

U.S. PATENT DOCUMENTS

| | | |
|---|---|---|
| 2009/0192532 A1* | 7/2009 | Spinnler ............... A61F 2/0063 606/153 |
| 2009/0198260 A1 | 8/2009 | Ford et al. |
| 2009/0216338 A1 | 8/2009 | Gingras et al. |
| 2009/0270999 A1 | 10/2009 | Brown |
| 2009/0276057 A1 | 11/2009 | Trabucco et al. |
| 2009/0281558 A1 | 11/2009 | Li |
| 2009/0299538 A1 | 12/2009 | Suzuki |
| 2009/0326676 A1 | 12/2009 | Dupic et al. |
| 2010/0003308 A1 | 1/2010 | Tapolsky et al. |
| 2010/0089409 A1 | 4/2010 | Bertagnoli |
| 2010/0094404 A1 | 4/2010 | Greenhalgh et al. |
| 2010/0104608 A1 | 4/2010 | Abuzaina et al. |
| 2010/0160375 A1 | 6/2010 | King |
| 2010/0286716 A1 | 11/2010 | Ford et al. |
| 2010/0312043 A1 | 12/2010 | Goddard |
| 2010/0318108 A1 | 12/2010 | Datta et al. |
| 2011/0063325 A1* | 3/2011 | Saunders ................. G09G 5/00 345/639 |
| 2011/0081397 A1* | 4/2011 | Skalla .................. A61F 2/0063 424/423 |
| 2011/0082330 A1 | 4/2011 | Deitch |
| 2011/0144667 A1 | 6/2011 | Horton et al. |
| 2011/0236460 A1 | 9/2011 | Stopek et al. |
| 2011/0238094 A1 | 9/2011 | Thomas et al. |
| 2011/0251699 A1 | 10/2011 | Ladet |
| 2011/0257666 A1 | 10/2011 | Ladet et al. |
| 2011/0264120 A1 | 10/2011 | Bayon et al. |
| 2011/0265283 A1 | 11/2011 | Duncan |
| 2011/0293688 A1 | 12/2011 | Bennett et al. |
| 2011/0320009 A1 | 12/2011 | Ladet et al. |
| 2012/0010637 A1 | 1/2012 | Stopek et al. |
| 2012/0016388 A1 | 1/2012 | Houard et al. |
| 2012/0029537 A1 | 2/2012 | Mortarino |
| 2012/0029540 A1 | 2/2012 | Adams |
| 2012/0053602 A1 | 3/2012 | Adzich et al. |
| 2012/0065727 A1 | 3/2012 | Reneker et al. |
| 2012/0082712 A1 | 4/2012 | Stopek et al. |
| 2012/0109165 A1 | 5/2012 | Mathisen et al. |
| 2012/0116423 A1 | 5/2012 | Gleiman et al. |
| 2012/0116425 A1 | 5/2012 | Intoccia et al. |
| 2012/0150204 A1 | 6/2012 | Mortarino et al. |
| 2012/0179175 A1 | 7/2012 | Hammell |
| 2012/0179176 A1 | 7/2012 | Wilson et al. |
| 2012/0239063 A1 | 9/2012 | Lee |
| 2012/0259348 A1 | 10/2012 | Paul |
| 2013/0060263 A1 | 3/2013 | Bailly et al. |

FOREIGN PATENT DOCUMENTS

| | | |
|---|---|---|
| EP | 1158082 A2 | 11/2001 |
| EP | 1674048 A1 | 6/2006 |
| EP | 2016956 A2 | 1/2009 |
| EP | 2314254 A2 | 4/2011 |
| EP | 2353545 A1 | 8/2011 |
| EP | 2404571 A1 | 1/2012 |
| FR | 2601371 A1 | 1/1988 |
| FR | 2857851 A1 | 1/2005 |
| FR | 2924330 A1 | 6/2009 |
| FR | 2929834 A1 | 10/2009 |
| FR | 2949687 A1 | 3/2011 |
| FR | 2949688 A1 | 3/2011 |
| FR | 2951069 A1 | 4/2011 |
| FR | 2953709 A1 | 6/2011 |
| WO | 9311805 A1 | 6/1993 |
| WO | 9806355 A1 | 2/1998 |
| WO | 9951163 A1 | 10/1999 |
| WO | 0180788 A2 | 11/2001 |
| WO | 0181667 A1 | 11/2001 |
| WO | 0217853 A2 | 3/2002 |
| WO | 0234304 A1 | 5/2002 |
| WO | 03007847 A1 | 1/2003 |
| WO | 2005028581 A1 | 3/2005 |
| WO | 2006020922 A2 | 2/2006 |
| WO | 2006036967 A1 | 4/2006 |
| WO | 2006040760 A2 | 4/2006 |
| WO | 2006102374 A2 | 9/2006 |
| WO | 2007025266 A2 | 3/2007 |
| WO | 2008127411 A1 | 10/2008 |
| WO | 2009031035 A2 | 3/2009 |
| WO | 2009075786 A1 | 6/2009 |
| WO | 2010043978 A2 | 4/2010 |
| WO | 2010043979 A2 | 4/2010 |
| WO | 2010093333 A1 | 8/2010 |
| WO | 2010129641 A1 | 11/2010 |
| WO | 2011007062 A1 | 1/2011 |
| WO | WO2011/026987 * | 3/2011 |
| WO | 2011038740 A1 | 4/2011 |
| WO | 2011117758 A2 | 9/2011 |
| WO | WO2012/007578 * | 1/2012 |
| WO | 2013098343 A1 | 7/2013 |

OTHER PUBLICATIONS

International Search Report for PCT/EP13/063643 dated Sep. 23, 2013 (4 pages).
Australian Examination report dated Feb. 27, 2017 in corresponding Australian Patent Application No. 2013283278, 3 pages.
Australian Examination Report dated Oct. 27, 2016 in corresponding Australian Patent Application No. 013283278, 3 pages.

* cited by examiner

HERNIA PROSTHESIS

CROSS-REFERENCE TO RELATED APPLICATIONS

This application is a National Stage Application of PCT/EP13/063643 under 35USC §371 (a), which claims priority of French Patent Application Serial No. 12/56206 filed Jun. 29, 2012, the disclosures of each of the above-identified applications are hereby incorporated by reference in their entirety.

The present invention relates to a prosthesis, for example a prosthesis for plugging hernias, comprising a mesh provided with a coloured peripheral skirt.

The abdominal wall in humans is composed of fat and muscles interconnected by fascias. It sometimes happens that a break in continuity occurs in the fascias, allowing part of the peritoneum to slip through and form a sac, or a hernia, containing either fat or part of the intestines. Hernias or incisional hernias (a hernia occurring through a parietal surgical scar) show themselves in the form of a bulge at the surface of the skin and are classed, for example, as umbilical or inguinal hernias or incisional hernias, depending on where they are located.

In order to repair a hernia defect, surgeons often fit a prosthesis in place which is made of synthetic mesh and replaces or strengthens the weakened anatomical tissues.

However, the effectiveness of the prosthesis, hence the ability to minimize the risks of recurrence, depends to a large extent on how well the prosthesis is fixed.

One method of hernia repair involves open surgery, with incision of the skin and then of the abdominal wall. However, in this type of surgery, the surgeon has little space to work in and poor visibility. It is therefore preferable to make available a prosthesis that is easy to position and fix.

Thus, particularly in the case of a hernia of the abdominal wall, it would be useful to have a prosthesis that can be positioned easily against the abdominal wall, in such a way that the surgeon can easily fix the prosthesis in an effective way despite the poor view of the operating site.

The present invention relates to a prosthesis that is able to be easily fixed, in such a way that the surgeon can fix it effectively and can do so despite the inherently poor view of the operating site.

The prosthesis according to the invention is useful for the treatment of a hernia defect of the abdominal wall.

A first aspect of the present invention relates to a prosthesis comprising:

at least one layer of a flexible mesh delimited by a peripheral outer edge, said mesh having a first colour, and at least one layer of porous material fixed to said mesh substantially along the perimeter of said peripheral outer edge, said layer of porous material being recessed at its central part, in such a way that it forms a sort of skirt extending from the peripheral outer edge of the mesh, or from a point set slightly back from this peripheral outer edge, towards the centre of the mesh, the skirt thus formed being substantially parallel to the plane of the mesh, said layer of porous material having a second colour, different from said first colour.

Within the meaning of the present application, a "mesh" is understood as an arrangement of biocompatible yarns, such as a knit, a woven fabric, a non-woven fabric, preferably open-worked, that is to say provided with pores that favour recolonization of tissue. Such a mesh can be bioresorbable, permanent or partially bioresorbable. It is sufficiently flexible to be folded up at the time of introduction into the abdominal cavity. The mesh can be made from one layer of textile or several layers of textiles. Such meshes are well known to a person skilled in the art. The mesh that can be used according to the invention can be supplied in any shape whatsoever, for example rectangular, square, circular, oval, etc., and can then be cut to suit the shape of the hernia defect. For example, the overall shape of the mesh can be circular or oval. Alternatively, the mesh can have a generally square shape or a rectangular shape.

Within the meaning of the present application, porous material is understood as a material having pores, voids or holes, promoting cell colonization.

The layer of porous material is fixed to the first mesh layer substantially along the perimeter of the peripheral outer edge of the mesh. Thus, the line of fixing of the layer of porous material can be situated either at the peripheral outer edge of the mesh or set slightly back, this fixing line being generally parallel to said perimeter.

The layer of porous material is recessed in its central part, in such a way that it forms a sort of skirt extending from the peripheral outer edge of the mesh, or from a point set slightly back from this peripheral outer edge, towards the centre of the mesh, the skirt thus formed being substantially parallel to the plane of the mesh.

The mesh and the layer of porous material are of different colours, a first colour for the mesh and a second colour for the layer of porous material. In one embodiment, the first colour and the second colour generate a contrast of 50% to 100%, preferably of 70% to 100%, according to the scale of contrast sensitivity defined for public buildings. In the present application, the contrast is determined according to the scale of contrast sensitivity (Functional Acuity Contrast Test) defined for public buildings by Dr Arthur Ginsburg, illustrated by Table I below:

TABLE I

| | Beige | White | Grey | Black | Brown | Pink | Purple | Green | Orange | Blue | Yellow | Red |
|---|---|---|---|---|---|---|---|---|---|---|---|---|
| | contrast in %, according to the scale of contrast sensitivity defined for public buildings | | | | | | | | | | | |
| Red | 78 | 84 | 32 | 38 | 7 | 57 | 28 | 24 | 62 | 13 | 82 | 0 |
| Yellow | 14 | 16 | 73 | 89 | 80 | 58 | 75 | 76 | 52 | 79 | 0 | |
| Blue | 75 | 82 | 21 | 47 | 7 | 50 | 17 | 12 | 56 | 0 | | |
| Orange | 44 | 60 | 44 | 76 | 59 | 12 | 47 | 50 | 0 | | | |
| Green | 72 | 80 | 11 | 53 | 18 | 43 | 6 | 0 | | | | |
| Purple | 70 | 79 | 5 | 56 | 22 | 40 | 0 | | | | | |
| Pink | 51 | 65 | 37 | 73 | 53 | 0 | | | | | | |
| Brown | 77 | 84 | 26 | 43 | 0 | | | | | | | |
| Black | 87 | 91 | 58 | 0 | | | | | | | | |

TABLE I-continued contrast in %, according to the scale of contrast sensitivity defined for public buildings

| | Beige | White | Grey | Black | Brown | Pink | Purple | Green | Orange | Blue | Yellow | Red |
|---|---|---|---|---|---|---|---|---|---|---|---|---|
| Grey | 69 | 78 | 0 | | | | | | | | | |
| White | 28 | 0 | | | | | | | | | | |
| Beige | 0 | | | | | | | | | | | |

As will be seen from Table I above, the first colour/second colour combinations suitable for the prosthesis of the invention can be chosen from among the following combinations: beige/red, beige/blue, beige/green, beige/purple, beige/pink, beige/brown, beige/black, beige/grey, white/red, white/blue, white/orange, white/green, white/purple, white/pink, white/brown, white/black, white/grey, grey/yellow, grey/black, black/yellow, black/orange, black/green, black/purple, black/pink, brown/yellow, brown/orange, brown/pink, pink/red, pink/yellow, pink/blue, purple/yellow, green/yellow, green/orange, orange/red, orange/yellow, orange/blue, blue/yellow, yellow/red.

In one embodiment, the first colour is white and the second colour is green: thus, the contrast generated by these two colours is 80%, as is indicated in Table I above.

In another embodiment, the first colour is beige and the second colour is blue: thus, the contrast generated by these two colours is 75%, as is indicated in Table I above.

The difference in colour between the layer of porous material and the mesh of the prosthesis according to the invention, in particular a contrast generated by the first colour and the second colour of 50% to 100% as defined above, is particularly advantageous given the poor view occasioned by the smallness of the working area: this difference in colour makes it possible, despite this poor view, to determine the presence of the layer of porous material, and therefore of the fixing means, thus showing the surgeon where to make the sutures for fixing the prosthesis to the abdominal wall.

As will become clear from the description below, the shape of the layer of porous material, its location at the periphery of the mesh, and its difference in colour in relation to the mesh, allow the surgeon, when implanting the prosthesis, to fix this layer of porous material effectively to the biological tissues, such as the peritoneum or the abdominal wall, for example. Indeed, in a first step, the surgeon very quickly sees the layer of porous material, because of the colour thereof, which differs from the colour of the mesh. In a second step, by virtue of the central recessed part of the layer of porous material, the surgeon very easily accesses the skirt formed by this layer and can easily manipulate the latter with the suitable fixing means, for example a resorbable or non-resorbable suture or staple, in order to fix the prosthesis in place. Thus, the surgeon is assured of fixing the prosthesis to the biological tissues, for example the abdominal wall or peritoneum, by means of the skirt of porous material, without any risk of touching and/or stapling the surrounding organs, for example the intestines, and without damaging the mesh forming the main body of the prosthesis.

Moreover, the porous structure of the layer of porous material permits good tissue integration of the skirt formed by this layer once the prosthesis has been implanted. Thus, in one embodiment, the layer of porous material has pores with an average size ranging from $1\times1$ mm$^2$ to $2\times2$ mm$^2$. In the present application, the size of the pores is measured according to the standard NF S94-801: 2007 "Reinforcement implants introduced by the vaginal route for the treatment of stress urinary incontinence and/or of prolapse of the pelvic organs—pre-clinical trials and clinical trials"—§5.3.3 Method b 10 specimens 100×50 mm.

Such an embodiment, in particular with pores having an average size ranging from $1\times1$ mm$^2$ to $2\times2$ mm$^2$, measured as indicated above, permits good visibility through the skirt, allowing the surgeon to see if part of a surrounding organ such as an intestinal loop is folded undesirably between the skirt and the biological tissues to which the skirt is to be fixed, and also permits good cell colonization of the skirt formed by the layer of porous material, all this while affording a sufficient amount of material for effective colour contrast between the mesh and the skirt, which contrast is directly perceivable by the surgeon at the time he has to fix the prosthesis.

Preferably, the layer of porous material is fixed continuously along said perimeter. The surgeon therefore knows that he can apply the sutures or the staples at any point on the skirt formed by the layer of recessed porous material, without having to look for a precise location.

In one embodiment of the invention, the mesh is a knit. By virtue of the meshwork of the knit, it is possible to obtain openworked faces that promote cell recolonization after implantation. The knit can be two-dimensional or three-dimensional.

Within the meaning of the present application, a two-dimensional knit is understood as a knit having two opposite faces linked to each other by meshes but devoid of a spacer giving it a certain thickness: such a knit can be obtained, for example, by knitting yarns on a warp knitting machine or raschel knitting machine using two guide bars. Examples of knitting two-dimensional knits suitable for the present invention are given in the document WO2009/071998.

According to the present application, a three-dimensional knit is understood as a knit having two opposite faces linked to each other by a spacer that gives the knit a significant thickness, said spacer itself being formed from additional linking yarns in addition to the yarns forming the two faces of the knit. Such a knit can be obtained, for example, on a double-bed warp knitting or raschel knitting machine using several guide bars. Examples of knitting three-dimensional knits suitable for the present invention are given in the documents WO99/05990, WO2009/031035 and WO2009/071998.

In one embodiment, the layer of porous material is a textile. The structure of the textile forming the layer of porous material may be identical to or different from the one forming the mesh.

The mesh and the layer of porous material can be made of a bioresorbable or non-bioresorbable material.

The bioresorbable material suitable for the production of the mesh and/or of the layer of porous material can be chosen from among the following bioresorbable materials: polylactic acid (PLA), polycaprolactones (PCL), polydioxanones (PDO), trimethylene carbonates (TMC), polyvinyl alcohol (PVA), polyhydroxyalkanoates (PHA), oxidized cellulose, polyglycolic acid (PGA), copolymers of these materials, and mixtures thereof.

The non-bioresorbable material suitable for the production of the mesh and/or of the layer of porous material can be chosen from among the following non-bioresorbable materials: polypropylenes, polyesters such as polyethylene terephthalates, polyamides, silicones, polyether ether ketone (PEEK), polyarylether ether ketone (PAEK) and mixtures thereof.

In one embodiment of the invention, the layer of porous material can be made from a gripping textile. Examples of gripping textile are described in the document WO/0181667. For example, with said gripping textile having a face provided with barbs, said face provided with barbs can be directed towards the outside of the prosthesis. Thus, the prosthesis can be fixed to the biological tissues, for example the abdominal wall, by virtue solely of the presence of the barbs that fasten themselves in these biological tissues. With such an embodiment, it is possible to dispense with a supplementary fixing step. It also dispenses with the need to use supplementary fixing means such as staples or sutures in the body of the patient.

In one embodiment of the invention, said mesh has the shape of a disc. Such an embodiment is suitable, for example, for the treatment of an umbilical hernia. In another embodiment, said mesh has the shape of a rectangle, with or without rounded corners. Such an embodiment is suitable, for example, for the treatment of a ventral hernia.

In one embodiment of the invention, that face of the mesh opposite the face having the layer of porous material is covered by an anti-adhesion coating.

Such a coating makes it possible in particular to avoid the formation of undesirable and serious post-surgical fibrous adhesions, for example when the prosthesis is implanted in an intraperitoneal location.

Within the meaning of the present application, "anti-adhesion" is to be understood as meaning a smooth and non-porous biocompatible material or coating that does not provide space for cell recolonization and preferably promotes the growth of a peritoneum.

Figure 2:
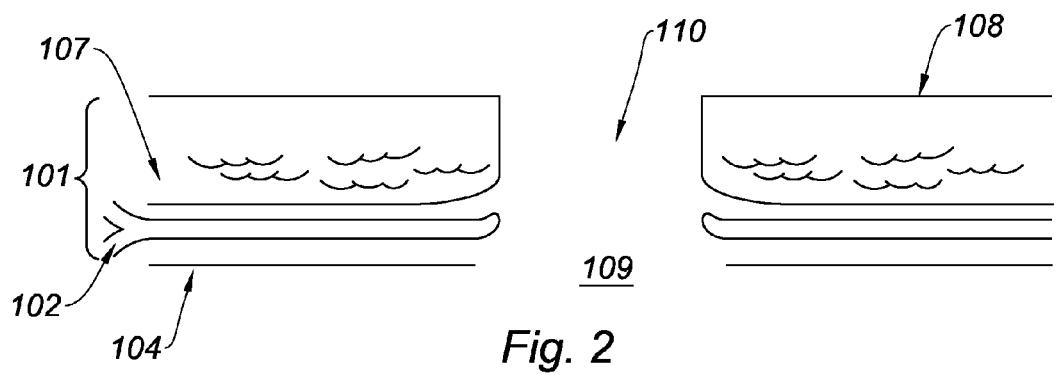
Figure 3:
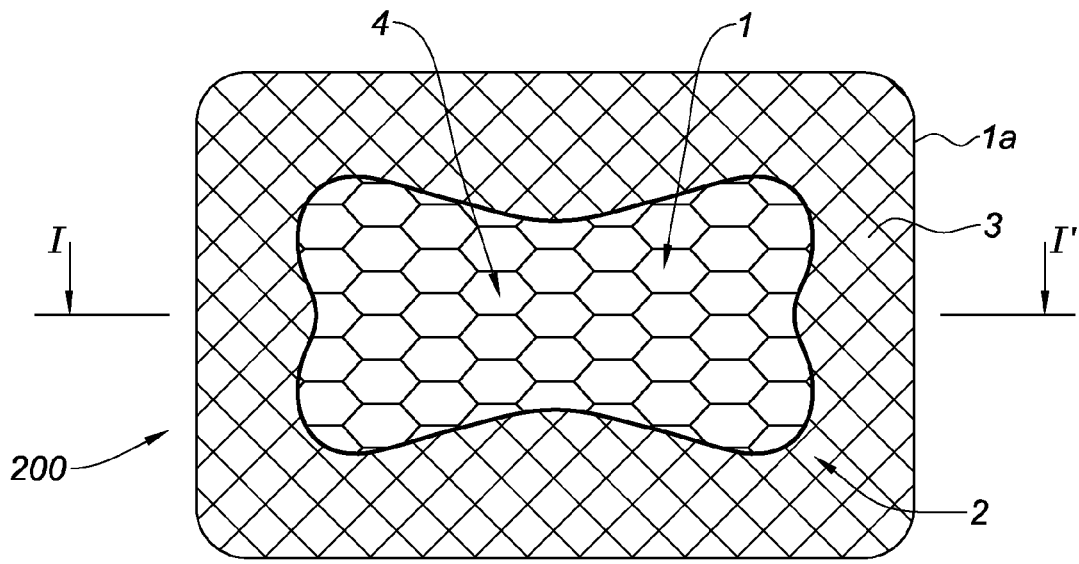
Figure 4:
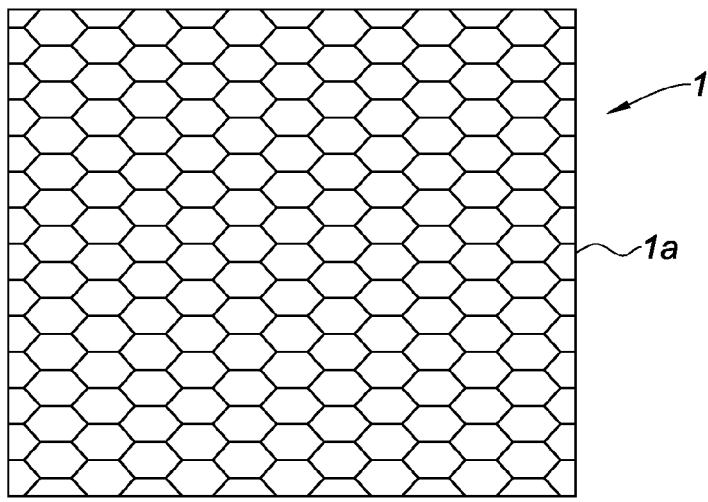
Figure 5:
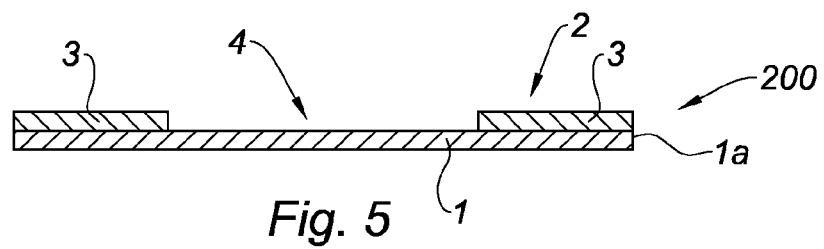
Figure 6:
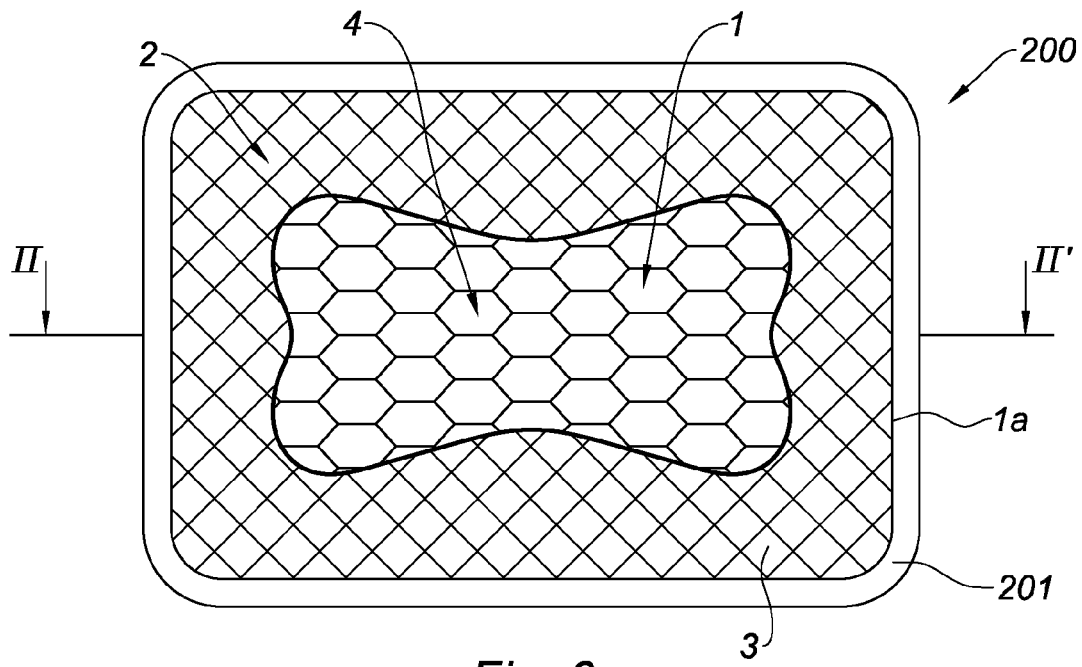
Figure 7:
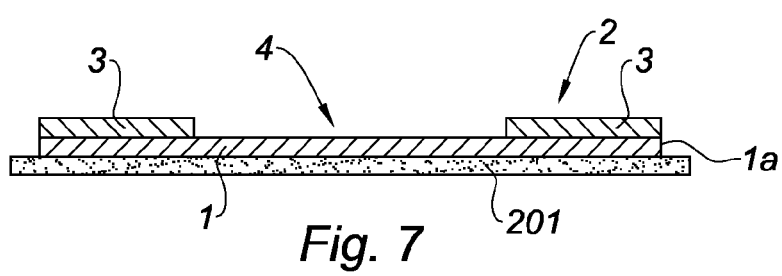
Figure 8:
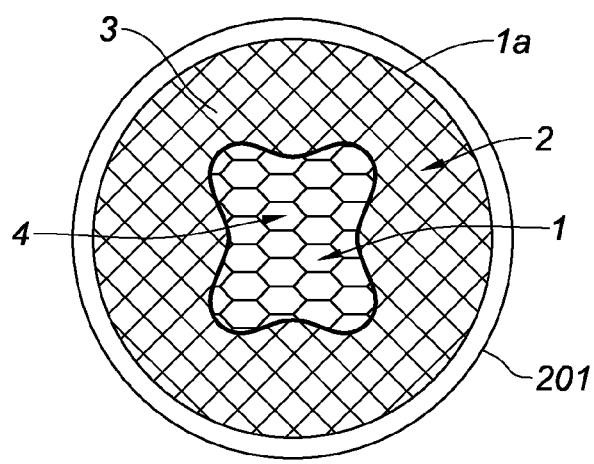
Figure 9:
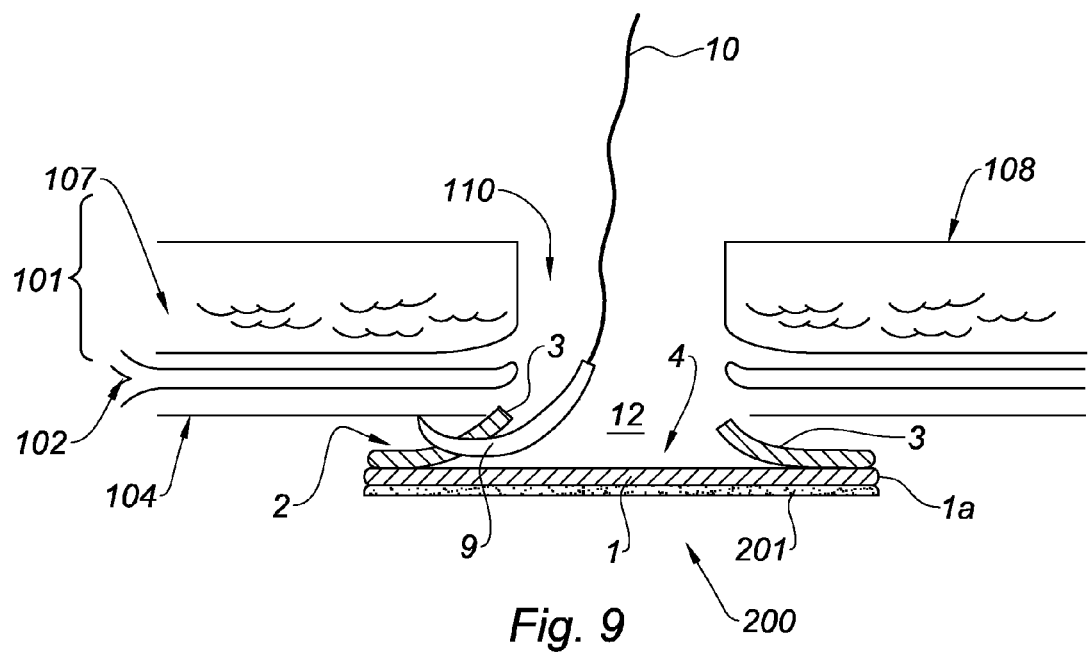
Figure 10:
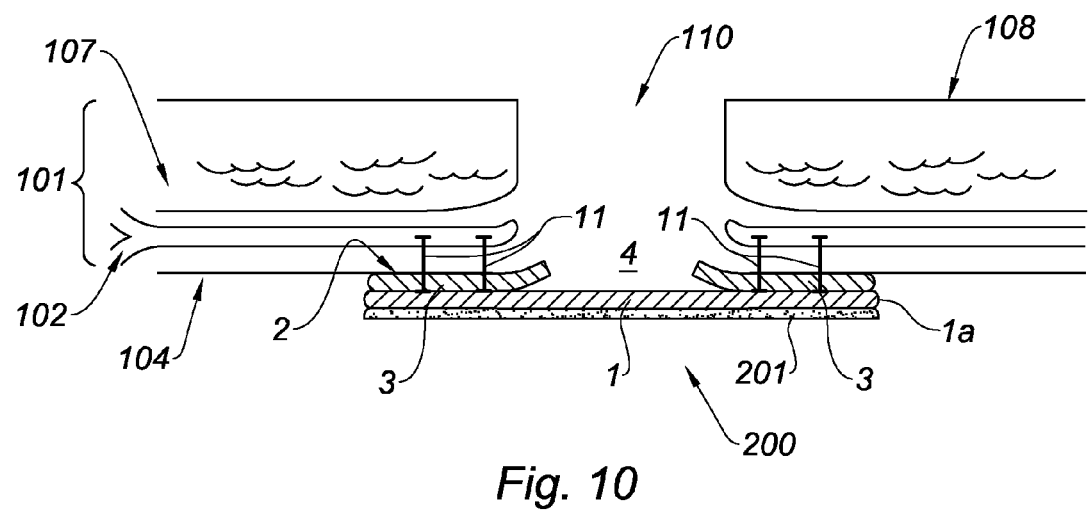
Figure 11:
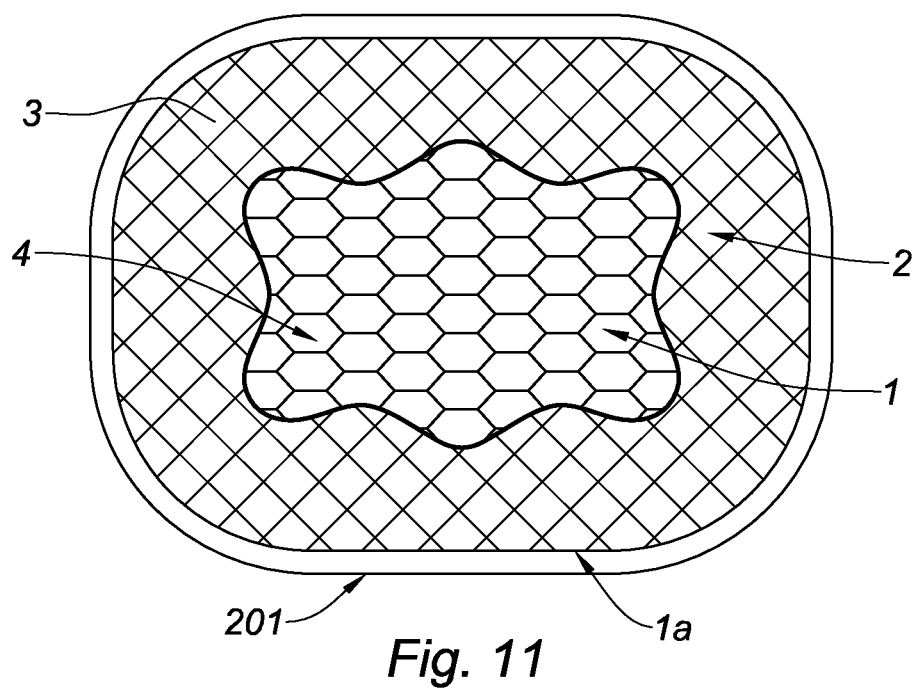

The present invention will become clearer from the following description and from the attached drawings, in which:

FIG. 1 is a sectional view of a median abdominal hernia,

FIG. 2 is a simplified view of the hernia from FIG. 1 once the surgeon has made an abdominal incision and has removed the hernial sac, FIG. 3 is a plan view of a first embodiment of a prosthesis according to the invention, FIG. 4 is a plan view of a mesh suitable for the production of the prosthesis from FIG. 3, FIG. 5 is a sectional view, in the plane I-I', of the prosthesis from FIG. 3, FIG. 6 is a plan view of a second embodiment of a prosthesis according to the invention, FIG. 7 is a sectional view, in the plane II-II', of the prosthesis from FIG. 6, FIG. 8 is a plan view of a third embodiment of a prosthesis according to the invention, FIG. 9 is a simplified sectional view showing the fixing of the prosthesis from FIG. 6, FIG. 10 is a sectional view of the prosthesis from FIG. 6 once it has been fixed to the biological tissues, just before closure of the abdominal incision by the surgeon, FIG. 11 is a plan view of a fourth embodiment of a prosthesis according to the invention.

FIG. 1 shows a hernia defect 100 of the abdominal wall 101, characterized by a break in continuity of the fascia 102 surrounding the rectus muscles 103 and by a passage through the peritoneum 104 forming a sac, the hernial sac 105, which contains either fat (greater omentum) or part of the viscera 106, and which thus exerts pressure on the fatty tissues 107 and lies flush with the skin 108. Treatment of a hernia defect 100 involves repositioning and maintaining the viscera 106 in the abdominal cavity 109.

FIG. 2 shows the hernia defect 100 from FIG. 1 once the surgeon has made an incision in the skin 108, the abdominal wall 101 and the peritoneum 104 and has reduced the hernial sac. The viscera are not shown in FIG. 2: they have been pushed back towards the abdominal cavity 109. By way of the incision 110 that he has made, the surgeon must now introduce into the abdominal cavity 109 a prosthesis intended to strengthen the abdominal wall, after which the incision 110 is closed by sutures, for example. In the case of an umbilical hernia, the size of the incision 110 is particularly small, for example of the order of 1 to 4 cm in diameter.

FIGS. 3 and 5 show a prosthesis 200 according to the invention, comprising a mesh layer 1 and a layer 2 of porous material, the mesh 1 having a first colour and the layer 2 of porous material having a second colour. In particular, the contrast between the first colour and the second colour is from 50% to 100%, preferably from 70% to 100%, according to the contrast sensitivity scale defined for public buildings, as shown by Table I above.

The mesh 1, shown on its own in FIG. 4, is composed of an arrangement of biocompatible yarns, such as a knit, woven fabric or non-woven fabric. It can be bioresorbable, permanent or partly bioresorbable. Generally, the mesh is openworked and contains pores for better tissue integration. This mesh 1 is sufficiently flexible to be folded up at the time of introduction of the prosthesis into the abdominal cavity 109 via the incision 110. However, the mesh is generally a textile that does not have an elasticity allowing it to spontaneously recover a deployed configuration when it has been folded. The mesh 1 can be composed of a layer of textile or of several layers of textiles. The textile can be a two-dimensional or three-dimensional textile. Such meshes are well known to a person skilled in the art and are not described in any more detail here.

The mesh 1 can be supplied in the form of a band that is cut to the dimensions of the defect that is to be treated. In the example shown in FIGS. 3 and 4, the mesh 1 has the shape of a rectangle delimited by a peripheral outer edge 1a. This shape of the mesh 1 is suitable, for example, for the treatment of a ventral hernia. In other embodiments, the shape of the mesh could be square, circular or oval.

The mesh 1 has a first colour: for example, the mesh 1 can be made from white yarns.

The layer 2 of porous material can be made of any porous biocompatible material giving it the necessary flexibility to be able to be gripped by the surgeon when implanting the prosthesis, as will be described below. Within the meaning of the present application, porous material is understood as a material having pores, voids or holes, promoting cell colonization.

The layer 2 of porous material is recessed in its central part 4, in such a way that it forms a peripheral skirt 3 attached to the mesh 1 along the peripheral outer edge 1a. The layer 2 of porous material can be fixed to the peripheral outer edge 1a by any means, such as bonding, welding, stitching, etc. The fixing line can be situated slightly set back from the perimeter of the peripheral outer edge 1a. As will become clear later, the skirt 3 thus formed is intended to help the surgeon fix the prosthesis 200 to the abdominal wall.

Preferably, the layer 2 of porous material, hence the skirt 3 formed by this layer, is fixed continuously along the perimeter of the peripheral outer edge 1a of the mesh. The surgeon can therefore make the attachment points, such as sutures or staples, needed for fixing the prosthesis 200 at any location of the skirt 3 formed by the layer 2 of porous material. His work is thus made easier.

The recessed central part 4 of the layer 2 of porous material can have any shape permitting access, to the face of the skirt 3 situated against the mesh 1, by the surgeon or by means of the fixing tools such as needle, staples, etc. Generally, the shape of the recessed central part 4 largely follows that of the peripheral outer edge of the mesh 1, or it can have a succession of wider and narrower parts, as is shown in FIG. 3. These wider and narrower parts can be distributed symmetrically along the perimeter of the peripheral outer edge 1a. The succession of these wider and narrower parts generates locating points for the surgeon and permits easier orientation of the prosthesis. For example, referring to FIG. 3, the narrower parts show the surgeon the corners of the prosthesis, whereas the wider parts indicate the sides of the prosthesis.

For example, the layer 2 of porous material is made of textile. The structure of the textile can be identical to or different from the one forming the mesh 1. The layer 2 of porous material has a second colour differing from the first colour of the mesh 1.

The first colour/second colour combinations suitable for the prosthesis of the invention can be chosen from among the following combinations: beige/red, beige/blue, beige/green, beige/purple, beige/pink, beige/brown, beige/black, beige/grey, white/red, white/blue, white/orange, white/green, white/purple, white/pink, white/brown, white/black, white/grey, grey/yellow, grey/black, black/yellow, black/orange, black/green, black/purple, black/pink, brown/yellow, brown/orange, brown/pink, pink/red, pink/yellow, pink/blue, purple/yellow, green/yellow, green/orange, orange/red, orange/yellow, orange/blue, blue/yellow, yellow/red.

In the example shown, with the first colour being white for example, the layer 2 of porous material, hence the skirt 3 formed by this layer, is green in colour. For example, the layer 2 of porous material can be made from green monofilament yarn.

Thus, referring to Table I above, the contrast generated by the white/green combination in the present example is 80%, according to the contrast sensitivity scale defined for public buildings.

In one embodiment, the layer 2 of porous material is made from a polyethylene terephthalate monofilament yarn, which is green and has a diameter of 0.09 mm, on a warp knitting machine with two guide bars, the yarns being threaded one full, one empty according to the following chart in accordance with ISO 11676:

bar 1: 1.0/0.1//
bar 2: 1.0/1.0/1.0/6.7//

The following properties of this porous textile have been determined as follows:

Mass per unit area (g/m$^2$): measured according to ISO 3801: 1977 <<Determination of mass per unit length and mass per unit area>>, 5 specimens 1 dm$^2$, Size of the pores (width×height) (mm): measured according to NF S94-801:2007 "Reinforcement implants introduced by the vaginal route for the treatment of stress urinary incontinence and/or of prolapse of the pelvic organs—pre-clinical trials and clinical trials"—§5.3.3 Method b 10 specimens 100×50 mm, Bursting strength (kPa): measured according to ISO 13938-2: 1999 "Textiles—Bursting properties of textiles—Pneumatic method for determining the bursting strength and bursting deformation"

Suture strength (N) in the warp direction and Suture strength (N) in the weft direction: measured according to NF S94-801: 2007 "Reinforcement implants introduced by the vaginal route for the treatment of stress urinary incontinence and/or of prolapse of the pelvic organs—pre-clinical trials and clinical trials"—§5.3.3 5 specimens 50×100 mm, USP 2/0 suture yarn, cross speed: 100 mm/min Tensile strength (N) in the warp direction and Tensile strength (N) in the weft direction: measured according to ISO 13934-1: 1999 "Determination of tensile strength and elongation", length between the jaws: 200 mm, cross speed: 100 mm/min, pre-charge: 2 N.

Tear strength (N) in the warp direction and Tear strength (N) in the weft direction: measured according to ISO 4674: 1977 "Textiles covered with rubber or plastic—Determination of the tear strength" Method A2, 5 specimens 75×225 mm, cross speed: 100 mm/min.

The results are the following:
Mass per unit area (g/m$^2$): 61±1
Size of the pores (width×height) (mm): 1.6×1.9
Bursting strength (kPa): 487±9
Suture strength (N) in the warp direction: 35±1
Suture strength (N) in the weft direction: 35±2
Tensile strength (N) in the warp direction: 205±6
Tensile strength (N) in the weft direction: 255±11
Tear strength (N) in the warp direction: 22±0
Tear strength (N) in the weft direction: 20±1

With such a textile, it is possible to obtain a layer 2 of porous material, hence a skirt 3 formed by this layer, permitting excellent cell recolonization once the prosthesis has been implanted, while at the same time generating an effective contrast between the white mesh 1 and said green skirt 3, in such a way that the surgeon immediately sees where he is to make the sutures when fixing the prosthesis to the abdominal wall. Moreover, a textile of this kind is sufficiently porous to ensure that the surgeon can easily detect if part of a surrounding organ, for example an intestinal loop, is folded undesirably between the skirt and the biological tissues to which the skirt is to be fixed. The structure of this textile thus makes it possible to reduce the risks of inadvertently damaging part of a surrounding organ when fixing the prosthesis in place.

In another embodiment, the mesh is produced with a polypropylene monofilament yarn of a beige colour, and the layer of porous material is produced with a polypropylene monofilament yarn of a blue colour. The contrast generated by these two colours, with reference to Table I above, is therefore 75%, according to the contrast sensitivity scale defined for public buildings, and allows the surgeon to quickly see where he has to arrange the fixation points.

In an embodiment, the layer 2 of porous material may be formed, for example, from a gripping textile, as described in WO/0181667. In this case, with said gripping textile having a face provided with barbs, said face provided with barbs can be positioned towards the outside of the prosthesis. Thus, when implanting the prosthesis, the latter can be fixed to the abdominal wall directly with the aid of the barbs fastening themselves in the abdominal wall, without the need to use additional sutures or staples.

The mesh 1 and the layer 2 of porous material can be made of bioresorbable material, non-bioresorbable material, or a combination of these materials.

In the present application, "bioresorbable" is understood as the characteristic whereby a material is absorbed by the biological tissues and disappears in vivo after a specified period of time which may vary, for example, from a day to several months, depending on the chemical nature of the material.

Thus, examples of bioresorbable materials suitable for the production of the mesh 1 and/or of the layer 2 of porous material of the prosthesis according to the invention are polylactic acid (PLA), polycaprolactones (PCL), polydioxanones (PDO), trimethylene carbonates (TMC), polyvinyl alcohol (PVA), polyhydroxyalkanoates (PHA), oxidized cellulose, polyglycolic acid (PGA), copolymers of these materials, and mixtures thereof. As bioresorbable material suitable for producing the mesh 1 and/or the layer 2 of porous material of the prosthesis according to the present invention, mention may be made of the polyester (glycolide, dioxanone, trimethylene carbonate) available commercially from Covidien under the trade name Biosyn® or the polyester (glycolide, caprolactone, trimethylene carbonate, lactide) available commercially from Covidien under the trade name Caprosyn®.

As non-bioresorbable materials suitable for producing the mesh 1 and/or the layer 2 of porous material of the prosthesis according to the present invention, mention may be made of polypropylenes, polyesters such as polyethylene terephthalates, polyamides, silicones, polyether ether ketone (PEEK), polyarylether ether ketone (PAEK) and mixtures thereof.

FIGS. 6 and 7 show a prosthesis 200 similar to the one in FIGS. 3 and 5, but in which that face of the mesh 1 opposite the one with the layer 2 of porous material, and thus with the skirt 3 formed by this layer, is covered with an anti-adhesion coating 201. An anti-adhesion coating of this kind makes it possible in particular to avoid the formation of serious and undesirable post-surgical fibrous adhesions; once the prosthesis 200 has been implanted, the face of the prosthesis 200 covered with the anti-adhesion coating 201 is situated opposite the abdominal cavity 109.

The anti-adhesion material or coating is chosen from among bioresorbable materials, non-bioresorbable materials and mixtures thereof. The non-bioresorbable anti-adhesion materials can be chosen from among polytetrafluoroethylene, polyethylene glycols, polysiloxanes, polyurethanes, and mixtures thereof.

Said anti-adhesion material or coating is preferably bioresorbable: the bioresorbable materials suitable for said anti-adhesion coating can be chosen from among collagens, oxidized celluloses, polyacrylates, trimethylene carbonates, caprolactones, dioxanones, glycolic acid, lactic acid, glycolides, lactides, polysaccharides, for example chitosans, polyglucuronic acids, hyaluronic acids, dextrans, and mixtures thereof.

The anti-adhesion coating makes it possible to protect the mesh 1 of the prosthesis 200, at least during the initial phase of healing, that is to say the mesh 1 is not exposed to inflammatory cells such as granulocytes, monocytes, macrophages or even the multi-nuclear giant cells that are generally activated by the surgery. Indeed, at least during the initial phase of healing, the duration of which can vary between 5 and 10 days approximately, only the anti-adhesion coating can be accessed by the various factors such as proteins, enzymes, cytokines or cells of the inflammatory line.

In the case where the anti-adhesion coating is made of non-resorbable materials, it thus protects the mesh 1 before and after implantation, throughout the period of implantation of the prosthesis 200.

Moreover, by virtue of the anti-adhesion coating, the fragile surrounding tissues such as the hollow viscera, for example, are protected particularly from the formation of serious and undesirable post-surgical fibrous adhesions.

In the case where the anti-adhesion material comprises a bioresorbable material, it is preferable to choose a bioresorbable material that is resorbed only after a few days, so as to ensure that the anti-adhesion coating can perform its function of protecting the intestine and the hollow organs during the days after the operation and until the cell recolonization of the prosthesis in turn protects the fragile organs.

The mesh 1 and the anti-adhesion coating 201 are sufficiently flexible to follow the successive deformations of the prosthesis 200 when the latter is introduced into the implantation site.

FIG. 8 shows a prosthesis 200 which is similar to the one in FIGS. 6 and 7 but which has a round shape. Such a prosthesis 200 is perfectly suitable, for example, for the treatment of an umbilical hernia. FIG. 11 shows a prosthesis which is similar to the one in FIGS. 6 and 7 but which has an oval shape.

The fixation of a prosthesis according to the invention, for example the prosthesis 200 in FIGS. 6 and 7, will now be described with reference to FIGS. 9 and 10, in the case of an intraperitoneal implantation.

After the incision 110 described in FIG. 2 has been made, the surgeon takes hold of the prosthesis 200 of FIG. 6, which is covered with an anti-adhesion coating 201 on that face of the mesh 1 opposite the one with the peripheral skirt 3 formed by the layer 2 of porous material, and uses his fingers to subject the prosthesis 200 to a stress by which it is folded up on itself. For reasons of clarity, the surgeon's fingers are not shown in FIGS. 9 and 10.

Once the prosthesis 200 is in the abdominal cavity 109, the surgeon relaxes the pressure that he was exerting on said prosthesis. The surgeon deploys the prosthesis 200 and spreads it out.

Once the prosthesis 200 is correctly positioned with respect to the hernia defect, the surgeon lifts part of the margins of the hernia defect and thus frees a working zone 12 in the vicinity of the prosthesis 200, delimited overall by the recessed central part 4 of the layer of porous material 2 (see FIG. 9). By virtue of the difference in colour between the mesh 1 and the layer 2 of porous material, and in particular by virtue of the contrast generated by this difference of colour, the surgeon immediately sees the skirt 3 formed by the layer 2 of porous material, and he can easily visualize the zone within which he will be able to easily work. Indeed, the difference in colour between the wide and narrow parts of the skirt 3, formed by the layer of porous material 2, and the mesh 1 defines a zone which shows the surgeon where to apply the sutures for fixing the prosthesis 200 to the abdominal wall. This fixing or suturing zone largely corresponds to the succession of wide and narrow parts (see FIG. 6) of the skirt 3 formed by the layer of porous material 2.

As is shown in FIG. 9, by virtue of the recessed central part 4 of the layer 2 of porous material, the surgeon has easy access to that face of the layer 2 of porous material situated against the mesh 1, and he lifts the skirt 3 formed by the layer 2 of porous material. He then proceeds to fix the prosthesis 200 to the biological tissues, using a needle 9 and a suture thread 10 to suture the skirt 3, formed by the layer of porous material 2, to the abdominal wall 101, 104. The surgeon can form one or more sutures 11 for fixing the prosthesis 200 to the abdominal wall, as is shown in FIG. 10.

The surgeon then simply has to close up the incision 110 in a conventional manner, for example by stitches.

The prosthesis according to the invention is particularly easy to fit in place, the surgeon being easily able to see the working zone and the layer 2 of porous material allowing the prosthesis to be fixed to the abdominal wall, despite the small dimensions of the implantation site. A prosthesis according to the invention is particularly suitable for the treatment of hernias of the abdominal wall. By virtue of its particular structure, the prosthesis according to the invention can be fixed to the abdominal wall in an effective way.

The invention claimed is:

1. A prosthesis comprising:
   at least one layer of a flexible mesh delimited by a peripheral outer edge, said mesh having a first color, and
   at least one layer of a porous material fixed to said mesh substantially along a perimeter of said peripheral outer edge, said layer of porous material including a recess at a central part, in such a way that said layer of porous material forms a skirt extending from the peripheral outer edge of the mesh, or from a point set slightly back from the peripheral outer edge, towards a center of the mesh, the skirt being substantially parallel to a plane of the mesh and including a succession of wider parts and narrower parts, the narrower parts indication corners of the peripheral outer edge and the wider parts indicating sides of the peripheral outer edge, said layer of porous material having a second color, different from said first color, wherein the first color and the second color generate a contrast of 50% to 100%, according to the scale of contrast sensitivity defined for public buildings.

2. The prosthesis according to claim 1, wherein said layer of porous material is fixed continuously along said perimeter.

3. The prosthesis according to claim 1, wherein said layer of porous material is a textile.

4. The prosthesis according to claim 3, wherein said textile is a gripping textile.

5. The prosthesis according to claim 4, wherein said gripping textile has a face provided with barbs, said face provided with barbs being directed towards an outside of the prosthesis.

6. The prosthesis according to claim 1 wherein a second face of the mesh opposite a first face having the layer of porous material is covered with an anti-adhesion coating.

7. The prosthesis according to claim 1 wherein said layer of porous material has pores with an average size ranging from $1 \times 1$ mm$^2$ to $2 \times 2$ mm$^2$.

8. The prosthesis according to claim 1, wherein the first color and the second color generate a contrast of 70% to 100%, according to the scale of contrast sensitivity defined for public buildings.

9. The prosthesis according to claim 1, wherein the first color and second color combination is selected from the group consisting of beige/red, beige/blue, beige/green, beige/purple, beige/pink, beige/brown, beige/black, beige/grey, white/red, white/blue, white/orange, white/green, white/purple, white/pink, white/brown, white/black, white/grey, grey/yellow, grey/black, black/yellow, black/orange, black/green, black/purple, black/pink, brown/yellow, brown/orange, brown/pink, pink/red, pink/yellow, pink/blue, purple/yellow, green/yellow, green/orange, orange/red, orange/yellow, orange/blue, blue/yellow, yellow/red.

10. The prosthesis according to claim 1, wherein the first color and second color combination is white/green.

11. The prosthesis according to claim 1, wherein the first color and second color combination is beige/blue.

12. The prosthesis according to claim 1, wherein the succession of wider parts and narrower parts is distributed symmetrically along the perimeter of the peripheral outer edge.

13. The prosthesis according to claim 1 wherein the porous material is non-bioresorbable.

14. A prosthesis for hernia repair comprising:
    at least one layer of a flexible mesh delimited by a peripheral outer edge, said mesh having a first color, and
    at least one gripping textile having a face provided with barbs, said at least one gripping textile fixed to said mesh substantially along a perimeter of said peripheral outer edge, said at least one gripping textile including a recess at a central part, in such a way that said at least one gripping textile forms a skirt extending from the peripheral outer edge of the mesh, or from a point set slightly back from the peripheral outer edge, towards a center of the mesh, the skirt being substantially parallel to a plane of the mesh and including a succession of wider parts and narrower parts, the narrower parts indicating corners of the peripheral outer edge and the wider parts indicating sides of the peripheral outer edge, said at least one gripping textile having a second color different from said first color, wherein the first color and the second color generate a contrast of 50% to 100% according to the scale of contrast sensitivity defined for public buildings.

15. The prosthesis according to claim 14, wherein a second face of the mesh opposite a first face having the at least one gripping textile is covered with an anti-adhesion coating.

16. The prosthesis according to claim 14, wherein said at least one gripping textile has pores with an average size ranging from $1 \times 1$ mm$^2$ to $2 \times 2$ mm$^2$.

17. The prosthesis according to claim 14, wherein the first color and the second color generate a contrast of 70% to 100%, according to the scale of contrast sensitivity defined for public buildings.

18. The prosthesis according to claim 14, wherein the first color and second color combination is selected from the group consisting of beige/red, beige/blue, beige/green, beige/purple, beige/pink, beige/brown, beige/black, beige/grey, white/red, white/blue, white/orange, white/green, white/purple, white/pink, white/brown, white/black, white/grey, grey/yellow, grey/black, black/yellow, black/orange, black/green, black/purple, black/pink, brown/yellow, brown/orange, brown/pink, pink/red, pink/yellow, pink/blue, purple/yellow, green/yellow, green/orange, orange/red, orange/yellow, orange/blue, blue/yellow, yellow/red.

19. The prosthesis according to claim 14, wherein the first color and second color combination is white/green.

20. The prosthesis according to claim 14, wherein the first color and second color combination is beige/blue.

21. The prosthesis for hernia repair of claim 14, wherein the first color/second color combination is selected from a group consisting of beige/red, beige/green, beige/purple, beige/pink, beige/brown, beige/black, beige/grey, white/red, white/orange, white/pink, white/brown, white/black, white/grey, grey/yellow, grey/black, black/yellow, black/orange, black/green, black/purple, black/pink, brown/yellow, brown/orange, brown/pink, pink/red, pink/yellow, pink/blue, purple/yellow, green/yellow, green/orange, orange/red, orange/yellow, orange/blue, blue/yellow, yellow/red.

22. The prosthesis according to claim 14, wherein said face provided with said barbs is directed towards an outside of the prosthesis.

* * * * *